United States Patent
Mladen et al.

(10) Patent No.: US 8,637,705 B2
(45) Date of Patent: Jan. 28, 2014

(54) AMPHIPHILIC OXALAMIDE ORGANOGELATORS DESIGNED FOR GELATION OF ORGANIC SOLVENTS, WATER AND HYDROCARBON COMMERCIAL FUELS

(75) Inventors: Žinić Mladen, Zagreb (HR); Makarević Janja, Zagreb (HR)

(73) Assignee: Rudjer Boskovic Institute, Zagreb (HR)

( * ) Notice: Subject to any disclaimer, the term of this patent is extended or adjusted under 35 U.S.C. 154(b) by 612 days.

(21) Appl. No.: 12/733,479

(22) PCT Filed: Sep. 4, 2008

(86) PCT No.: PCT/HR2008/000031
§ 371 (c)(1),
(2), (4) Date: Mar. 2, 2010

(87) PCT Pub. No.: WO2009/030964
PCT Pub. Date: Mar. 12, 2009

(65) Prior Publication Data
US 2010/0218414 A1   Sep. 2, 2010

(30) Foreign Application Priority Data
Sep. 4, 2007   (HR) .............................. P 20070379 A

(51) Int. Cl.
*C07C 231/00* (2006.01)

(52) U.S. Cl.
USPC ....................................................... 564/133

(58) Field of Classification Search
None
See application file for complete search history.

(56) References Cited

FOREIGN PATENT DOCUMENTS

WO   WO 2009/030964 A2   3/2009

OTHER PUBLICATIONS

Mecinovic et al. (Bioorganic & Medicinal Chemistry Letters, 2009, 19, 6192).*
Petyunin et al. (Khimiko-Farmatsevticheskii Zhurnal, 1988, 22, 1329).*
English translation of Petyunin et al. (Khimiko-Farmatsevticheskii Zhurnal, 1988, 22, 1329).*
STN abstract of Petyunin et al. (Khimiko-Farmatsevticheskii Zhurnal, 1988, 22, 1329).*
J. Jung et al., "Self-Assembly of a Sugar-Based Gelator in Water: Its Remarkable Diversity in Gelation Ability and Aggregate Structure," *Langmuir*, 2001, vol. 17, pp. 7229-7232.
N. Fujita et al., Chapter 15: "Design and Function of Low Molecular-Mass Organic Gelators (LMOGs) Rearing Steroid and Sugar Groups," *Molecular Gels: Materials with Self-Assembled Fibrillar Networks* (Eds.: R. G. Weiss et al.), 2006, pp. 553-575.
O. Gronwald et al., "Gelators for organic liquids based on self-assembly: a new facet of supramolecular and combinatorial chemistry," *Current Opinion in Colloid & Interface Science* 7, 2002, pp. 148-156.
S. Shinkai et al., "Sugar-Integrated Gelators of Organic Solvents," *Chem. Eur. J.*, 2001, vol. 7, No. 20, pp. 4328-4334.
K. Hanabusa et al., "Small Molecular Gelling Agents to Harden Organic Liquids: Alkylamide of N-Benzyloxycarbonyl- L-valyl-L-valine," *J Chem. Soc., Chem. Commun.*, 1993, pp. 390-392.
V. Čaplar et al., "Positionally Isomeric Organic Gelators: Structure—Gelation Study, Racemic versus Enantiomeric Gelators, and Solvation Effects," *Chem. Eur. J.*, 2010, vol. 16, pp. 3066-3082.
*Mosby's Medical Dictionary*, 8th edition, 2009, Elsevier, definition of "starch mucilage," obtained from URL http://medical-dictionary.thefreedictionary.com/p/mucilage on Mar. 1, 2013.
Bhatiacharya et al., First report of phase selective galation of oil from oil/water mixtures. Possible implications toward containing oil spills. Chem. Commun., 2001, pp. 185-186.
Caplar et al., Chiral Gelators Constructed from 1 1-Aminoundecanoic (AUDA), Laurie and Amino Acid Units. Synthesis, Gelling Properties and Preferred Gelation of Racemates vs. the Pure Enantiomers, Eur. J. Org. Chem, 2004. pp. 4048-4059.
De Loos et al.. Design and Application of Self-Assembled Low Molecular Weight Hydrogels, Eur. J. Org. Chem., 2005, pp. 3615-3631.
Estroff et al.. Water Gelation by Small Organic Molecules. Chemical Reviews, 2004, 1201-17, vol. 104. No. 3.
Fages et al., Systematic Design of Amide- and Urea-Type Gelators with Tailored Properties, Top Curr Chem, 2005, pp. 77-131, vol. 256.
Khatua et al., Spontaneous Formation of Gel Emulsions in Organic Solvents and Commercial Fuels Induced by a Novel Class of Amino Acid Derivatized Surfactants, Langmuir, 2005, pp. 109-114, vol. 21.
Makarevic et al.. Chiral Bis(tyrosinol) and Bis(p-hydroxyphenylglycinol) Oxalamide Gelators. Influence of Aromatic Groups and Hydrogen Bonding on Gelation Properties, Croatica Chemica Acta, 2004, pp. 403-414. vol. 77, No. 1-2.
PCT International Search Report, PCT/HR2008/000031. dated Mar. 10, 2009.
PCT Written Opinion, PCT/HR2008/000031, 2009.
Sangeetha et al., Supramolecular gels: Functions and uses, Chem. Soc. Rev., 2005, pp. 821-836, vol. 34.
Suzuki et al., Powerful low-molecular-weight gelators based on L-valine and L-isoleucine with various terminal groups, New J. Chem., 2006. pp. 1184-1191, vol. 30.
Terech et al., Low Molecular Mass Gelators of Organic Liquids and the Properties of Their Gels, Chem. Rev. 1997, pp. 3133-3159, vol. 97.

(Continued)

*Primary Examiner* — Johann R Richter
*Assistant Examiner* — Jennifer C Sawyer
(74) *Attorney, Agent, or Firm* — Nixon Peabody LLP; Jeffrey L. Costellia

(57) ABSTRACT

The compounds of general formula (I) wherein: $R^1$ is hydrogen, phenyl, $C_{1-6}$ alkyl which can be further substituted with $R^3$, $R^3$ is 5- or 6-membered aromatic or heteroaromatic ring system which can be further substituted with benzyl or hydroxyl groups; $R^2$ is $OR^4$, $NHR^4$, $R^4$ is hydrogen, $C_{1-6}$ alkyl or benzyl n is an integer from 1 to 12 or the salts of compounds mentioned which can form gels with commercial fuels, organic solvents and water.

(I)

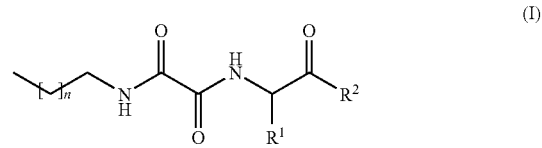

16 Claims, No Drawings

(56) References Cited

OTHER PUBLICATIONS

Trivedi et al., Cation-Induced Supramolecular Isomerism in the Hydrogen-Bonded Network of Secondary Ammonium Monocarboxylate Salts: A New Class of Organo Gelator and Their Structures, Crystal Growth & Design. 2006, pp. 2114-2121. vol. 6. No. 9.

Trivedi et al., Instant Gelation of Various Organic Fluids Including Petrol at Room Temperature by a New Class of Supramolecular Gelators, Chem. Mater., 2006. pp. 1470-1478, vol. 18.

Trivedi et al., Structure-Property Correlation of a New Family of Organogelators Based on Organic Salts and Their Selective Gelation of Oil from Oil/Water Mixtures, Chem. Eur. J., 2004, pp. 5311-5322, vol. 10.

Suzuki et al., new Gemini organogelators linked by osalyl amide: organogel fonnation and their thermal stabilities. Tetrahedron Letters, 2003. pp. 6841-6843, vol. 44.

Linton et al., Oxamyl dipeptide caspase inhibitors developed for the treatment of stroke, Bioorganic & Medicinal Chemistry Letters, 2004, pp. 2685-2691, vol. 14, No. 10.

Coe Seth et al., Molecular Symmetry and the Design of Molecular Solids: The Oxalamide Functionality as a Persistent Hydrogen Bonding Unit, Journal of the American Chemical Society, 1997, pp. 86-93, vol. 119, No. 1.

* cited by examiner

AMPHIPHILIC OXALAMIDE ORGANOGELATORS DESIGNED FOR GELATION OF ORGANIC SOLVENTS, WATER AND HYDROCARBON COMMERCIAL FUELS

FIELD OF INVENTION

The present invention relates to compounds which are capable of forming gels with commercial fuels, appropriate organic solvents and water, and to, methods of preparing these compounds. The invention also relates to the gels formed by these compounds, methods for making them and use of the gels in various applications.

Organogels have great potential for industrial applications due to their diversity in the structures and physical properties. Particular interest is in pharmaceutical industry for drug delivery, food and cosmetic industry, tissue engineering, electrooptic/photonic devices, as sensors or organic templates for the preparation of inorganic materials, etc. Gelation of commercial fuels and hazardous organic solvents and liquids can be useful for development of safety transport technology.

BACKGROUND ART

Investigation of gel formation by low molecular weight organogelators has attracted considerable interest in last 15 years. Some of the reviews are publicised (P. Terech et al, *Chem. Rev.*, 97, 3133-3159 (1997), L. A. Estroff et al, *Chem. Rev.* 104, 1201-1217 (2004), F. Fages et al, *Top. Curr. Chem.*, 256, 77-131 (2005), M. Neralagatta et al, *Chem. Soc. Rev.*, 34, 821-836 (2005), M. de Loos, et al, *Eur. J. Org. Chem.* (2005) 3615-3631).

First paper about selective oil gelation from oil/water mixtures with potential application in oil transport accident rehabilitations was reported by S Bhattacharya et al, *Chem. Commun.*, (2001) 185.

Some other publications describe investigation of commercial fuel gelation (D. R. Trivedi et al, *Chem. Mater.*, 18, 1470-1478 (2006); D. R., Trivedi et al, *Chem. Eur. J.* 2404, 10, 5311-5322; D. R. Trivedi et al, *Crystal Growth & Design.* 6(9):2114:2121, 200; M. Suzuki et. al, *New J. Chem.*, 30, 1184-1191, 2006; D. Khatua et al, *Langmuir* 21, 109:114, 2005)

In our earlier publication (V. Čaplar et al, *Eur. J. Org. Chem.*, 2004(19), 4048-4059) we tested gelation properties of some alkylaminoundecanoic acid derivatives with oil (Diesel), water and appropriate organic solvents.

DETAILED DESCRIPTION OF INVENTION

The present invention relates to the new amphyphilic oxalamide derivatives which are capable of forming gels with commercial fuels. In addition, these compounds can form gels with water and some organic solvents.

The present invention relates to the compounds of general formula (I):

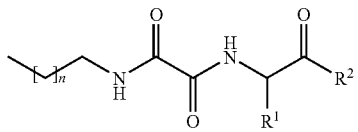

wherein:
$R^1$ is hydrogen, phenyl, $C_{1-6}$ alkyl which can be further substituted with $R^3$ $R^3$ is a 5- or 6-membered aromatic or heteroaromatic ring system which can be further substituted with benzyl or hydroxy groups
$R^2$ is $OR^4$, $NHR^4$
$R^4$ is hydrogen, $C_{1-6}$ alkyl or benzyl
n is an integer from 1 to 12
or a salt thereof.

Organogelators of general formula (I) can form gels by dissolution of a compound in a tested solvent and cooling the resulting solution to the room temperature. This procedure causes gel formation, which is macroscopical manifestation of supramolecular self-assembly of certain organic molecules to the nanoscale gel network.

The compounds of general formula (I), especially amide derivatives, can form gels at very low concentrations.

In the present invention, the term "organogelator" refers to any low molecular weight compound (such as the compounds of general formula (I)) which is able to form gel in appropriate solvent. The compound is dissolved by heating and the gel is formed by cooling this solution.

In the present specification "$C_1$-$C_6$ alkyl" refers to (I)) straight or branched hydrocarbon chains having one to six carbon atoms. Examples of alkyl moiety are methyl, ethyl, n-propyl, isopropyl, t-butyl, n-butyl and n-hexyl.

Salts of the compounds of general formula (I) include inorganic salts, ammonia salts and salts of substituted amines.

If a chiral centre is present in compounds of the present invention, all forms of such isomers are intended to be covered herein. Compounds of the invention containing a chiral centre may be used as entantiomers, racemic mixtures or enantiomerically enriched mixtures.

The term "aromatic moiety" in the context of the present specification refers to aromatic ring systems having 5 to 10 carbon atoms incorporated in one or two rings. Examples of aromatic moieties are benzene, naphthalene, biphenyl ring systems etc.

"Heteroaromatic" refers to aromatic ring systems as defined above but in which one or more carbon atoms is replaced by a nitrogen, oxygen or sulphur atom. Examples of heteroaromatic ring systems are indole, pyridine, imidazole, indazole, benzimidazole, quinoline, isoquinoline, benzthiazole, benzoxazole, etc.

In selected compounds of general formula (I) independently or in any combination:
$R^2$ is OH or $NHR^4$
n is integer from 2 to 10
Selected salts of compounds of general formula (I) are $Na^+$ and $K^+$.
In preferred compounds of general formula (I) n is 4 to 10 and $R^2$ is $NH_2$.
Preferred salts of compounds of general formula (I) are $Na^+$ salts.
Particularly preferred compounds, according to general formula (I), include:

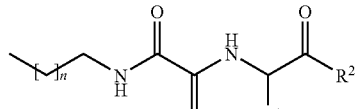

1 n = 2, $R^1$ = $CH_2CH(CH_3)_2$, $R^2$ = OMe
2 n = 2, $R^1$ = $CH_2CH(CH_3)_2$, $R^2$ = OH
3 n = 2, $R^1$ = $CH_2CH(CH_3)_2$, $R^2$ = $O^-Na^+$
4 n = 2, $R^1$ = $CH_2CH(CH_3)_2$, $R^2$ = $NH_2$
13 n = 10, $R^1$ = $CH_2CH(CH_3)_2$, $R^2$ = OMe
14 n = 10, $R^1$ = $CH_2CH(CH_3)_2$, $R^2$ = OH
15 n = 10, $R^1$ = $CH_2CH(CH_3)_2$, $R^2$ = $O^-Na^+$
16 n = 10, $R^1$ = $CH_2CH(CH_3)_2$, $R^2$ = $NH_2$
5 n = 4, $R^1$ = $CH_2CH(CH_3)_2$, $R^2$ = OMe
6 n = 4, $R^1$ = $CH_2Ph$, $R^2$ = OMe
7 n = 4, $R^1$ = $CH_2CH(CH_3)_2$, $R^2$ = OH
8 n = 4, $R^1$ = $CH_2Ph$, $R^2$ = OH
9 n = 4, $R^1$ = $CH_2CH(CH_3)_2$, $R^2$ = $O^-Na^+$
10 n = 4, $R^1$ = $CH_2Ph$, $R^2$ = $O^-Na^+$
11 n = 4, $R^1$ = $CH_2CH(CH_3)_2$, $R^2$ = $NH_2$
12 n = 4, $R^1$ = $CH_2Ph$, $R^2$ = $NH_2$ e.g. following compounds:
1. N-butyloxalamido-L-leucine methyl ester
2. N-butyloxalamido-L-leucine
3. N-butyloxalamido-L-leucine sodium salt
4. N-butyloxalamido-L-leucinamide
5. N-hexyloxalamido-L-leucine methyl ester
6. N-hexyloxalamido-L-phenylalanine methyl ester
7. N-hexyloxalamido-L-leucine
8. N-hexyloxalamido-L-phenylalanine
9. N-hexyloxalamido-L-leucine sodium salt
10. N-hexyloxalamido-L-phenylalanine sodium salt
11. N-hexyloxalamido-L-leucinamide
12. N-hexyloxalamido-L-phenylalaninamide
13. N-dodecyloxalamido-L-leucine methyl ester
14. N-dodecyloxalamido-L-leucine
15. N-dodecyloxalamido-L-leucine sodium salt
16. N-dodecyloxalamido-L-leucinamide Preferred compounds of the invention are prepared according to the following scheme:

$R^3$ is 5- or 6-membered aromatic or heteroaromatic ring system which can be further substituted with benzyl or hydroxyl groups;
$R^4$ is $C_{1-6}$ alkyl or benzyl
n is an integer from 1 to 12.

Compounds of general formula (Ia) can be prepared from the compounds with general formula (II)

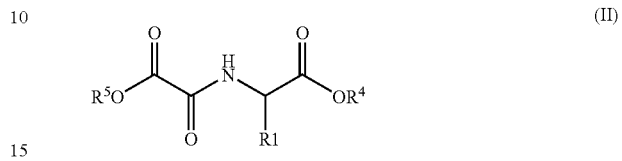

wherein:
$R^1$ is hydrogen, phenyl, $C_{1-6}$ alkyl which can be further substituted with $R^3$

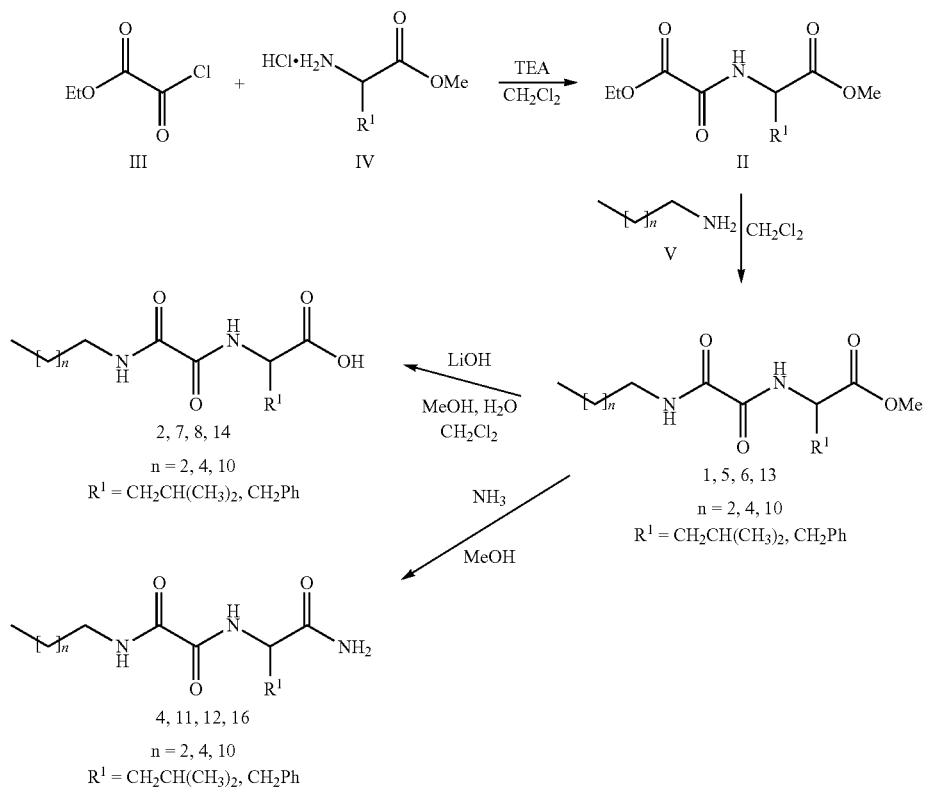

Compounds of general formula (I), where $R^2$ is $OR^4$, can be presented as esters of general formula (Ia)

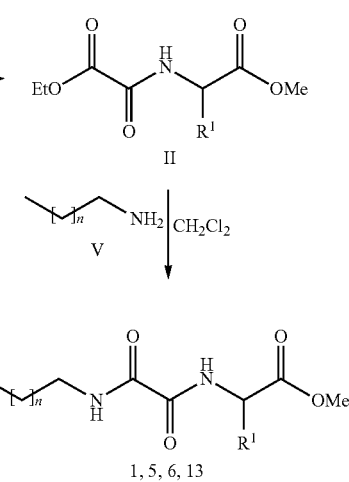

wherein:
$R^1$ is hydrogen, phenyl, $C_{1-6}$ alkyl which can be further substituted with $R^3$ $R^3$ is 5- or 6-membered aromatic or heteroaromatic ring system which can be further substituted with benzyl or hydroxyl groups;
$R^4$ is $C_{1-6}$ alkyl or benzyl
$R^5$ is $C_{1-6}$ alkyl or benzyl
by an aminolysis with compounds of general formula (V):

$$CH_3\text{---}(CH_2)_n\text{---}CH_2\text{---}NH_2 \qquad (V)$$

wherein n is an integer from 1 to 12.

The reaction is performed by stirring the solution of compounds with general formula (II) and compounds with general formula (V) in an organic solvent at room temperature.

Compounds of general formula (II) can be prepared from compounds of general formula (IV):

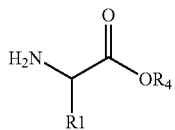

(IV)

wherein:
$R^1$ is hydrogen, phenyl, $C_{1-6}$ alkyl which can be further substituted with $R^3$
  $R^3$ is 5- or 6-membered aromatic or heteroaromatic ring system which can be further substituted with benzyl or hydroxyl groups;
$R^4$ is $C_{1-6}$ alkyl or benzyl
or from a salt thereof, whereby salt can be hydrochloride or tosylate
by an acylation with compounds of general formula (III):

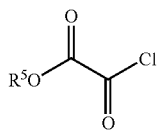

III wherein:
$R^5$ is alkyl or benzyl.

Acylation reaction can be carried out in organic solutions by dropwise addition of solution of compounds with general formula (III) to a solution of compounds with general formula (IV) and TEA at temperature −10-0° C. After that the reaction mixture is allowed to warm up to room temperature and stirred overnight.

Compounds of general formula (I), in which $R^2$ is OH, can be presented as compounds of general formula (Ib):

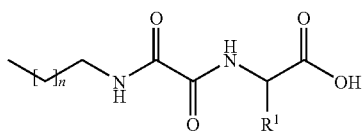

(Ib)

wherein:
$R^1$ is hydrogen, phenyl, $C_{1-6}$ alkyl which can be further substituted with $R^3$
  $R^3$ is 5- or 6-membered aromatic or heteroaromatic ring system which can be further substituted with benzyl or hydroxyl groups;
n is an integer from 1 to 12.

Compounds of general formula (Ib) can be prepared from the corresponding esters of general formula (Ia). The conversion of ester groups into carboxylic acids can be achieved by any known method, for example by hydrolysis of alkyl esters using lithium hydroxide solution or, alternatively, by hydrogenolysis of benzyl esters. In this reaction a solution of ester is hydrogenated over a suitable catalyst (typically palladium/carbon). Suitable protection and deprotection methodologies can be found, for example, in *Protecting Groups in Organic Synthesis*, by Theodor W. Greene and Peter G. M. Wuts, published by John Wiley & Sons Inc.

Compounds of general formula (I), in which $R^2$ is $NHR^6$, can be presented as compounds of general formula (Ic):

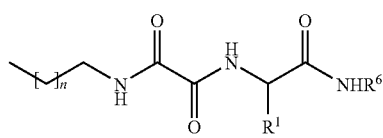

(Ic)

wherein:
$R^1$ is hydrogen, phenyl, $C_{1-6}$ alkyl which can be further substituted with $R^3$
  $R^3$ is 5- or 6-membered aromatic or heteroaromatic ring system which can be further substituted with benzyl or hydroxyl groups;
$R^6$ is hydrogen, $C_{1-6}$ alkyl or benzyl
n is an integer from 1 to 12.

Compounds of general formula (Ic) can be prepared from the corresponding esters of general formula (Ia) by the aminolysis reaction with the compounds of general formula (VI)

$$R^6-NH_2 \quad (VI)$$

wherein $R^6$, is hydrogen, $C_{1-6}$ alkyl or benzyl.

The conversion of ester group into carbamoyl group can be achieved by known methods, for example by reaction with saturated $NH_3$/MeOH or with solution of substituted amines.

Compounds of general formula (I) are capable of forming gels when heated in appropriate solvent, followed by cooling to room temperature. Alternatively, gel can be formed by dissolving organogelator in one organic solvent, followed by mixing this solution with another solvent.

Therefore, this invention relates also to the gels formed by the compounds of formula (I) or a salt thereof mixed with solvents. It also relates to the methods for preparing such gels from compounds of formula (I) or a salt thereof and solvents as well as the use of these gels in various applications.

Solvents can be commercial fuels like petrol, diesel etc. Alternatively, solvents can be $H_2O$ or organic solvents such as DMSO, DMF, EtOH, $CH_3CN$, THF, $CH_2Cl_2$, acetone, toluene, p-xylene, tetraline, decaline or mixtures thereof.

Chemical Synthesis of the Compounds with General Formula (I)

General

Reagents were purchased from Aldrich, Fluka, Kemika, Merck and Sigma, and were used without further purification. All solvents were purified and dried according to standard procedures. The reactions were monitored by thin layer chromatography (TLC) on Merck Kieselgel HF254 plastic sheets and spots were made visible using a UV lamp (254 nm) or $I_2$ vapours. Prepared compounds were purified chromatographically by preparative T.L.C. using silica gel Merck $HF_{254}$ and by column chromatography using silica 0.063-0.2 mm (Merck). Reaction yields are not optimised. NMR spectra were recorded on a Bruker Avance spectrometer at 300/75 MHz with tetramethylsylane (TMS) as an internal standard. Chemical shifts (δ) were given in ppm, coupling constants (J) in Hz. Spin multiplicities; s (singlet), d (doublet), t (triplet), q (quadruplet), p (pentet) and m (multiplet). IR spectra were taken in KBr pellets on ABB Bomen MB 102 FTIR-spectrometer, wave numbers (v) are reported in $cm^{-1}$. Optical rotations were measured on an Optical Activity AA-10 Automatic Polarimeter in a 1 dm cell at 589 nm; concentrations were given in g/100 ml.

1. General Procedure for Preparation of N-alkyl, N'-L-methylleucyl(phenylalanyl) oxalamides (Ia)

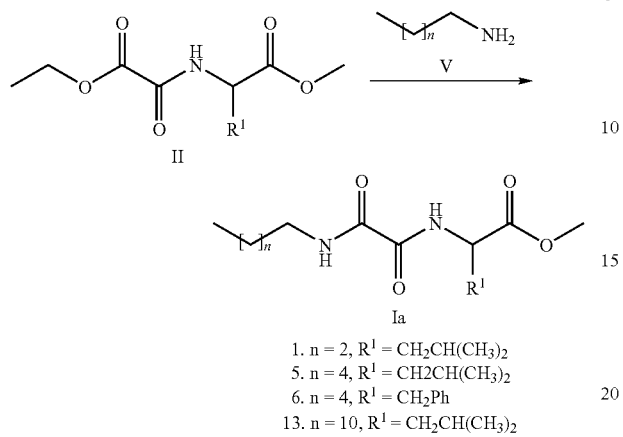

1. n = 2, R$^1$ = CH$_2$CH(CH$_3$)$_2$
5. n = 4, R$^1$ = CH2CH(CH$_3$)$_2$
6. n = 4, R$^1$ = CH$_2$Ph
13. n = 10, R$^1$ = CH$_2$CH(CH$_3$)$_2$ a) Preparation of N-(ethoxyoxalyl)-L-leucine(phenpylalanine)methyl ester (II); To a cooled (0° C.) solution of hydrochloride of amino acid IV (1 mmol) and TEA (2 mmol) in dry CH$_2$Cl$_2$ (10 ml) a solution of oxalyl chloride III (1 mmol) in dry CH$_2$Cl$_2$ (5 ml) was added dropwise during the 15' minutes. The reaction mixture was stirred for 30 min at 0° C. and 20 hours at room temperature. Afterwards CH$_2$Cl$_2$ (10 ml) was added and the mixture was washed successively with 5% HCl, 5% NaHCO$_3$ and water. The organic layer was dried over Na$_2$SO$_4$ and the solvent removed under reduced pressure. The ester II obtained in this way was used without additional purification.

b) To the solution of N-(ethoxyoxalyl)-L-leucine(phenylalanine)methyl ester (II) in dry CH$_2$Cl$_2$ alkylamine V was added and the reaction mixture was stirred for 3 days at room temperature. The product was purified by crystallisation (CH$_2$Cl$_2$—light petroleum) or preparative TLC chromatography (EtOAc-light petroleum, 100:25).

EXAMPLE 1

N-butyloxalamido-L-leucine Methyl Ester (1)

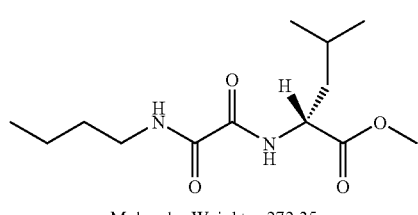

Molecular Weight = 272.35
Molecular Formula = C13H24N2O4

To the solution of N-(ethoxyoxalyl)-L-leucine methyl ester (II) (0.270 g, 1.01 mmol) in dry CH$_2$Cl$_2$ (10 ml) n-butylamine (0.110 ml, 1.113 mmol) was added and the reaction mixture was stirred for 3 days at room temperature. The product was purified by crystallisation (CH$_2$Cl$_2$—light petroleum) and by preparative TLC chromatography (EtOAc-light petroleum, 200:50). Yield: 78.7%; [α]$_D$=−13 (c1, CH$_2$Cl$_2$); $^1$H NMR (DMSO-d$_6$): δ 8.94 (1H, d, J=8.3, NH$_{Leu}$), 8.77 (1 H, t, J=5.7, NH$_{butyl}$), 4.36 (1H, ddd, J=3.6, J=8.3, J=11.1, CH$_{α, Leu}$), 3.63 (3H, s, OCH$_3$), 3.18-3.09 (2 H, m, CH$_2$N), 1.86-1.78, 1.59-1.49, 1.48-1.39, 1.31-1.19 (1H, 2H, 2H, 2H, 4 m, CH$_{β, Leu}$, CH$_{2(β, Leu)}$, CH$_{2, butyl}$), 0.89-0.83 (9 H, CH$_{3(γ, Leu)}$ and CH$_{3, butyl}$), $^{13}$C NMR (DMSO-d$_6$): δ 171.9 (COOMe), 160.3, 159.4 (CON), 52.0 (OCH$_3$), 50.4 (CH$_{α, Leu}$), 38.9, 38.5 (CH$_{2 (β, Leu)}$, CH$_2$N$_{butyl}$), 30.7, 19.5 (CH$_{2, butyl}$), 24.3, 22.8, 21.0 (CH$_{γ, Leu}$, CH$_{3, δ, Leu}$), 13.5 CH$_{3, butyl}$); IR: 3300, 1749, 1652, 1521.

EXAMPLE 2

N-hexyloxalamido-L-leucine Methyl Ester (5)

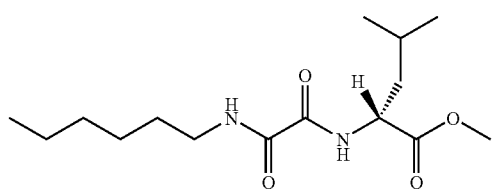

Molecular Weight = 300.40
Molecular Formula = C15H28N2O4

To the solution of N-(ethoxyoxalyl)-L-leucine methyl ester (II) (1.066 g, 4.346 mmol) in dry CH$_2$Cl$_2$ (40 ml) n-hexylamine (0.64 ml, 4.968 mmol) was added and the reaction mixture was stirred for 3 days at room temperature. The product was purified by crystallisation (CH$_2$Cl$_2$—light petroleum) and by preparative TLC chromatography (EtOAc-light petroleum, 200:50). Yield: 70%; [α]$_D$=−12 (c1, CH$_2$Cl$_2$); NMR (DMSO-d$_6$): δ 8.93 (1 H, d, J=8.4, NH$_{Leu}$), 8.76 (1 H, t, J=5.8, NH$_{hexyl}$), 4.36 (1H, ddd, J=3.5, J=8.4, J=10.6, CH$_{α, Leu}$), 3.63 (3 H, s, OCH$_3$), 3.16-3.08 (2 H, m, CH$_2$N), 1.86-1.77, 1.59-1.50, 1.49-1.41, 1.31-1.18 (1 H, 2H, 2 H, and 4 H, 4 m, CH$_{β, Leu}$, CH$_{2 (β, Leu)}$, CH$_{2, hexyl}$), 0.88, 0.84 (6 H, 2 d, J=5.9, CH$_{3(γ, Leu)}$), 0.86 (3 H, t, J=6.9, CH$_{3, hexyl}$), $^{13}$C NMR (DMSO-d$_6$): δ 172.4 (COOMe), 160.8, 159.8 (CON), 52.5 (OCH$_3$), 50.9 (CH$_{α, Leu}$), 39.4, 39.3 (CH$_{2(β, Leu)}$, CH$_2$N), 31.4, 29.1, 26.4, 22.5 (CH$_{2, hexyl}$), 24.7, 23.3, 21.5 (CH$_{γ, Leu}$, CH$_{3, δ, Leu}$), 14.3 CH$_{3, hexyl}$); IR: 3294, 1745, 1687, 1653, 1525.

EXAMPLE 3

N-hexyloxalamido-L-phenylalanine Methyl Ester (6)

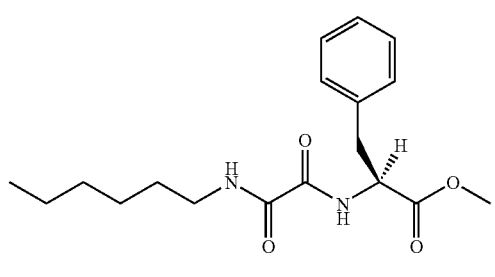

Molecular Weight = 334,42
Molecular Formula = C18H26N2O4

To the solution of N-(ethoxyoxalyl)-L-phenylalanine methyl ester (II) (4.900 g, 17.544. mmol) in dry CH$_2$Cl$_2$ (60 ml) n-hexylamine (2.32 ml, 17.562 mmol) was added and the reaction mixture was stirred for 3 days at room temperature.

The product was purified by preparative TLC chromatography (EtOAc-light petroleum, 200:50). Yield: 75%; NMR (DMSO-$d_6$): δ 8.92 (1 H, d, J=8.5, $NH_{Phe}$), 8.71 (1 H, t, J=6.0, $NH_{hexyl}$), 7.32-7.10 (5 H, m, $CH_{arom}$), 4.57 (1H, dt, J=5.9, J=8.5, $CH_{\alpha, Phe}$), 3.64 (3 H, s, $OCH_3$), 3.17-3.01 (4 H, m, $CH_2N$ and $CH_{2(\beta, Phe)}$), 1.49-1.32, 1.32-1.08 (2 H and 4 H, 2m, $CH_{2, hexyl}$), 0.85 (3 H, t, J=6.8, $CH_{3, hexyl}$), $^{13}C$ NMR ($CDCl_3$): δ 170.7 (COOMe), 159.6, 159.0 (CON), 136.4 ($C_{arom}$), 129.2, 128.8, 127.3 ($CH_{arom}$), 53.7, 52.5 ($CH_{\alpha, Phe}$ and $OCH_3$), 39.7, 37.8 ($CH_{2 (\beta, Phe}$, and $CH_2N$), 31.4, 29.1, 26.5, 22.5 ($CH_{2, hexyl}$), 14.0 $CH_{3, hexyl}$).

EXAMPLE 4

N-dodecyloxalamido-L-leucine Methyl Ester (13)

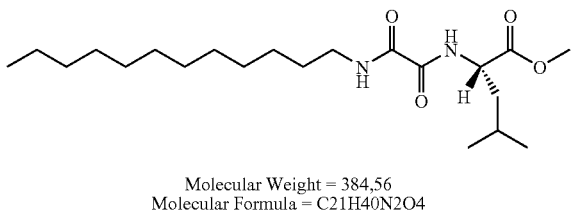 [SMILES: CCCCCCCCCCCCNC(=O)C(=O)N[C@@H](CC(C)C)C(=O)OC]

Molecular Weight = 384,56
Molecular Formula = C21H40N2O4

To the solution of N-(ethoxyoxalyl)-L-leucine methyl ester (II) (0.372 ml, 1.517 mmol) in dry $CH_2Cl_2$ (20 ml), n-dodecylamine (0.35 ml, 1.522 mmol) was added and the reaction mixture was stirred for 3 days at room temperature. The product was purified by crystallisation ($CH_2Cl_2$—light petroleum) and by preparative TLC chromatography (EtOAc-light petroleum, 200:50). Yield: 70.3%; $[\alpha]_D$=−9.5 (c1, $CH_2Cl_2$); $^1H$ NMR (DMSO-$d_6$): δ 8.93 (1 H, d, J=8.1, $NH_{Leu}$), 8.76 (1 H, t, J=5.6, $NH_{dodecyl}$), 4.39-4.32 (1H, m, $CH_{\alpha, Leu}$), 3.63 (3 H, s, $OCH_3$), 3.12 (2 H, q, J=6.6, $CH_2N$), 1.89-1.75, 1.61-1.50, 1.49-1.39 (1 H, 2 H, 2 H, 18 H, 4 m, $CH_{\gamma, Leu}$, $CH_{2 (\beta, Leu)}$, $CH_{2, dodecyl}$), 0.90-0.82 (9 H, m, $CH_{3(\gamma, Leu)}$ and $CH_{3, dodecyl}$); $^{13}C$ NMR (DMSO-$d_6$): δ 172.4 (COOMe), 160.8, 159.8 (CON), 52.5 ($OCH_3$), 50.9 ($CH_{\alpha, Leu}$) 39.4, 39.3 ($CH_{2 (\beta, Leu)}$, $CH_2N_{dodecyl}$), 31.8, 29.51, 29.47, 29.45, 29.42, 29.17, 29.14, 29.10, 26.8, 22.5 ($CH_{2, dodecyl}$), 24.8, 23.3, 21.5 ($CH_{\gamma, Leu}$, $CH_{3, o, Leu}$), 14.4 $CH_{3, dodecyl}$); IR: 3300, 1750, 1656, 1524.

2. General Procedure for Preparation of N-alkyl, N'-L-leucyl-oxalamides (Ib)

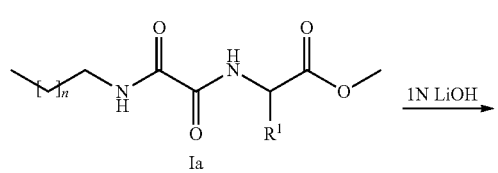

Ia
1 n = 2, $R^1$ = $CH_2CH(CH_3)_2$
5 n = 4, $R^1$ = $CH_2CH(CH_3)_2$
6 n = 4, $R^1$ = $CH_2Ph$
13 n = 10, $R^1$ = $CH_2CH(CH_3)_2$

1N LiOH →

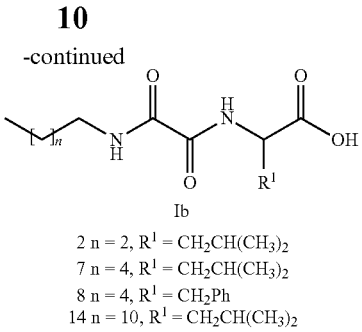

Ib
2 n = 2, $R^1$ = $CH_2CH(CH_3)_2$
7 n = 4, $R^1$ = $CH_2CH(CH_3)_2$
8 n = 4, $R^1$ = $CH_2Ph$
14 n = 10, $R^1$ = $CH_2CH(CH_3)_2$

To the solution of ester Ia in MeOH and $CH_2Cl_2$ 1N LiOH was added and the solution was stirred at room temperature overnight. The solvent was evaporated, the residue was dissolved in $H_2O$ and the solution was acidified with 1N HCl. The product was extracted with EtOAc and organic layer was washed with $H_2O$ and dried with $Na_2SO_4$. The solvent was evaporated at the reduced pressure to give solid product.

EXAMPLE 5

N-butyloxalamido-L-leucine (2)

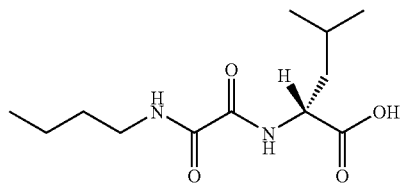

Molecular Weight = 258,32
Molecular Formula = C12H22N2O4

To the solution of N-butyloxalamido-L-leucine methyl ester (1) (0.247 g, 0.907 mmol) in MeOH (3 ml) and $CH_2Cl_2$ (1 ml) 1N LiOH (1.4 ml) was added and the solution was stirred at room temperature overnight. The solvent was evaporated, the residue was dissolved in $H_2O$ and the solution was acidified with 1N HCl. The product was extracted with EtOAc, organic layer was washed with $H_2O$ and dried with $Na_2SO_4$. The solvent was evaporated at the reduced pressure to give solid product. Yield: 92.2%: $[\alpha]_D$=−12 (c1, $CH_2Cl_2$); $^1H$ NMR (DMSO-$d_6$): δ 12.83 (1 H, s br, COOH), 8.77 (1 H, t, J=6.1, $NH_{butyl}$), 8.73 (1 H, d, J=8.6, $NH_{Leu}$), 4.28 (1H, ddd, J=10.5, J=8.6, J=3.4, $CH_{\alpha, Leu}$), 3.14 (2 H, q, J=6.7, $CH_2N$), 1.88-1.15 (7 H, m, $CH_\alpha$, $CH_{2(\beta, Leu)}$, $CH_{2, butyl}$), 0.91-0.82 (9 H, m, $CH_{3 (o, Leu)}$ and $CH_{3, butyl}$); $^{13}C$ NMR (DMSO-$d_6$): δ 173.6 (COOH), 160.6, 160.0 (CON), 50.9 ($CH_{\alpha, Leu}$), 39.6, 39.0 ($CH_{2(\beta, Leu)}$, $CH_{2, butyl}$), 31.3, 20.0 ($CH_{2, butyl}$), 24.9 ($CH_\gamma$), 23.4, 21.5 ($CH_{3(o, Leu)}$), 14.1 ($CH_{3, butyl}$); IR: 3314, 1745, 1656, 1519.

EXAMPLE 6

N-hexyloxalamido-L-leucine (7)

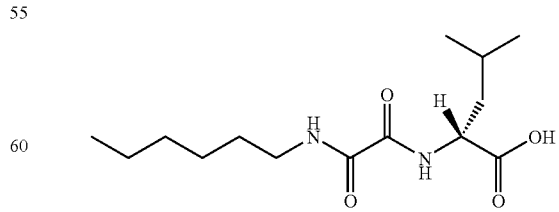

Molecular Weight = 286,37
Molecular Formula = C14H26N2O4

To the solution of N-hexyloxalamido-L-leucine methyl ester (5) (0.378 g, 1.258 mmol) in MeOH (2.5 ml) and CH$_2$Cl$_2$ (1 ml) 1N LiOH (1.9 ml) was added and the solution was stirred at room temperature overnight. The solvent was evaporated, the residue was dissolved in H$_2$O and the solution was acidified with 1N HCl. The product was extracted with EtOAc, organic layer was washed with H$_2$O and dried with Na$_2$SO$_4$. The solvent was evaporated at the reduced pressure to give solid product. Yield; 99%: [α]$_D$=−14 (c1, CH$_2$Cl$_2$); $^1$H NMR (DMSO-$_6$): δ 12.79 (1 H, s br, COOH), 8.78 (1 H, t, J=6.1, NH$_{hexyl}$), 8.73 (1 H, d, J=8.6 NH$_{Leu}$), 4.28 (1H, ddd, J=10.4, J=8.6, J=3.3, CH$_{α, Leu}$), 3.17-3.07 (2 H, m, CH$_2$N), 1.88-1.12 (11 H, m, CH$_{α, Leu}$, CH$_{2(β, Leu)}$, CH$_{2, hexyl}$), 0.91-0.82 (9 H, m, CH$_{3(σ, Leu)}$ and CH$_{3,hexyl}$); $^{13}$C NMR (DMSO-$_6$): δ 173.6 (COOH), 160.6, 160.0 (CON), 50.9 (CH$_α$), 39.6, 39.3 (CH$_{2(β, Leu)}$, CH$_{2, butyl}$), 31.4, 29.1, 26.5, 22.5 (CH$_{2, hexyl}$), 24.9 (CH$_γ$), 23.4, 21.5 (CH$_{3(σ, Leu)}$), 14.3 (CH$_3$, hexyl); IR: 3297, 1725, 1658, 1523.

EXAMPLE 7

N-hexyloxalamido-L-phenylalanine (8)

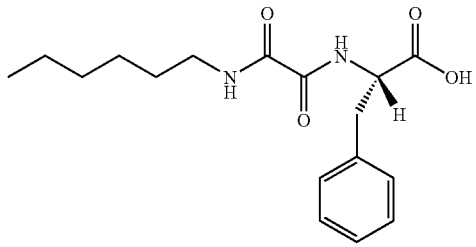

Molecular Weight = 320,39
Molecular Formula = C17H24N2O4

To the solution of N-hexyloxalamido-L-phenylalanine methyl ester (6) (0.043 g, 0.129. mmol) in MeOH (1 ml) and CH$_2$Cl$_2$ (0.2 ml) 1N LiOH (0.2 ml) was added and the solution was stirred at room temperature overnight. The solvent was evaporated, the residue was dissolved in H$_2$O and the solution was acidified with 1N HCl. The product was extracted with EtOAc, organic layer was washed with H$_2$O and dried with Na$_2$SO$_4$. The solvent was evaporated at the reduced pressure to give solid product. Yield: 60.6%; $^1$H NMR (DMSO-d$_6$): δ 13.0 (1H, s br, COOH), 8.69 (1 H, t, J=5.9, NH$_{hexyl}$), 8.66 (1 H, d, J=8.6, CH$_{α, Phe}$), 7.82-7.17 (5 H, m, CH$_{arom}$), 4.57 (1H, dt, J=4.7, J=8.6, CH$_{α, Phe}$), 3.19-3.03 (4 H, m, CH$_2$N and CH$_{2(β, Phe)}$), 148-1.36, 1.30-1.14 (2 H and 6 H, 2m, CH$_{2, hexyl}$), 0.85 (3 H, t, J=6.8, CH$_{3, hexyl}$), $^{13}$C NMR (DMSO-d$_6$): δ 172.0 (COOH), 159.8, 159.3 (CON), 137.5 (C$_{arom}$), 129.0, 128.2, 126.4 (CH$_{arom}$), 53.5 (CH$_{α, Phe}$), 38.8, 35.7 (CH$_{2 (β, Phe)}$ and CH$_2$N), 30.8, 28.5, 25.9, 22.0 (CH$_{2, hexyl}$), 13.8 CH$_{3, hexyl}$).

EXAMPLE 8

N-dodecyloxalamido-L-leucine (15)

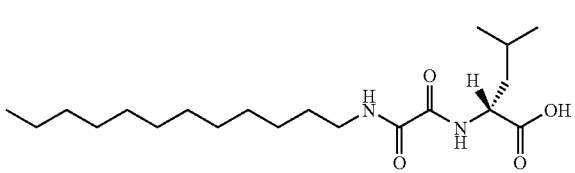

Molecular Weight = 370,54
Molecular Formula = C20H38N2O4

To the solution of N-dodecyloxalamido-L-leucine methyl ester (13) (0.345 g, 0.897 mmol) in MeOH (2.5 ml) and CH$_2$Cl$_2$ (0.7 ml) 1N LiOH (1.4 ml) was added and the solution was stirred at room temperature overnight. The solvent was evaporated, the residue was dissolved in H$_2$O and the solution was acidified with 1N HCl. The product was extracted with EtOAc, organic layer was washed with H$_2$O and dried with Na$_2$SO$_4$. The solvent was evaporated at the reduced pressure to give solid product. Yield: 99%; [α]$_D$=−9 (c1, CH$_2$Cl$_2$); $^1$H NMR (DMSO-$_6$): δ 12.79 (1 H, s br, COOH), 8.77 (1 H, t, J=6.0, NH$_{dodecyl}$), 8.71 (1 H, d, J=8.6, NH$_{Leu}$), 4.27 (1H, ddd, J=10.0, J=8.6, J=3.5, CH$_{α, Leu}$), 3.12 (2 H, q, J=6.7, CH$_2$N), 1.87-1.12 (23 H, m, CH$_{α,Leu}$, CH$_{2(β, Leu)}$, CH$_{2, dodecyl}$), 0.90-0.82 (9 H, m, CH$_{3(γ, Leu)}$ and CH$_{3, dodecyl}$); $^{13}$C NMR (DMSO-$_6$): δ 173.6 (COOH), 160.6, 159.9 (CON), 50.9 (CH$_{α, Leu}$), 39.6, 39.3 (CH$_{2(β, Leu)}$, CH$_{2, dodecyl}$), 31.8, 29.51, 29.48, 29.46, 29.41, 29.18, 29.15, 29.12, 26.8, 22.6 (CH$_{2, dodecyl}$), 24.9 (CH$_α$), 23.4, 21.5 (CH$_{3 (γ, Leu)}$), 14.4 (CH$_{3, dodecyl}$); IR: 3313, 1745, 1656, 1519.

3. General Procedure for Preparation of N-alkyl, N'-L-leucylamide-oxalamides (Ic)

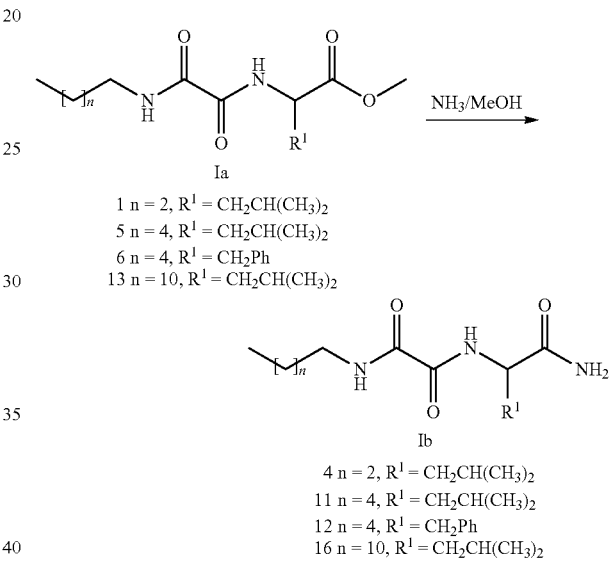

Ia 1 n = 2, R$^1$ = CH$_2$CH(CH$_3$)$_2$
5 n = 4, R$^1$ = CH$_2$CH(CH$_3$)$_2$
6 n = 4, R$^1$ = CH$_2$Ph
13 n = 10, R$^1$ = CH$_2$CH(CH$_3$)$_2$

Ib 4 n = 2, R$^1$ = CH$_2$CH(CH$_3$)$_2$
11 n = 4, R$^1$ = CH$_2$CH(CH$_3$)$_2$
12 n = 4, R$^1$ = CH$_2$Ph
16 n = 10, R$^1$ = CH$_2$CH(CH$_3$)$_2$

The solution of ester (Ia) in CH$_2$Cl$_2$ and conc. NH$_3$/MeOH was kept for 7 days at 4-8° C. The precipitate was filtered off, washed with MeOH and dried under reduced pressure or the solvent was evaporated at reduced pressure.

EXAMPLE 9

N-Butyloxalamido-L-leucylamide (4)

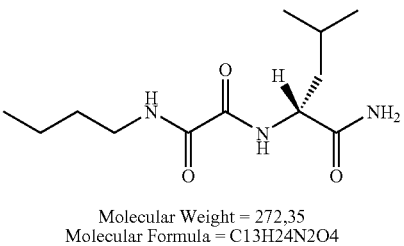 [SMILES: CCCCNC(=O)C(=O)N[C@H](CC(C)C)C(N)=O]

Molecular Weight = 272,35
Molecular Formula = C13H24N2O4

The solution of N-butyloxalamido-L-leucine methyl ester (1) (0.380 g, 1.395 mmol) it CH$_2$Cl$_2$ (1 ml) and conc. NH$_3$/MeOH (35 ml) was kept for 7 days at 4-8° C. The precipitate was filtered off, washed with MeOH. Yield: 89%; $^1$H NMR (DMSO-d$_6$): δ 8.78 (1 H, t, J=6.0, NH$_{butyl}$), 8.36 (1 H, d, J=9.0, $NH_{Leu}$), 7.48, 7.11 (2×1 H, 2 s, $CONH_2$), 4.28 (1H, dt, J=9.3, J=4.0, $CH_{\alpha, Leu}$), 3.21-3.04 (2 H, m, $CH_2N$), 1.72-1.14 (7 H, m, $CH_\alpha$, $CH_{2(\beta, Leu)}$, $CH_{2, butyl}$), 0.96-0.71 (9 H, m, $CH_{3(\gamma, Leu)}$ and $CH_{3, butyl}$); $^{13}C$ NMR (DMSO-$d_6$): δ 173.6 ($CONH_2$), 160.04, 160.01 (CON), 51.8 ($CH_\alpha$), 41.4, 39.0 ($CH_{2(\beta, Leu)}$, $CH_{2, butyl}$), 31.2, 20.0 ($CH_{2, butyl}$), 24.8 ($CH_\alpha$) 23.5, 21.9 ($CH_{3(\beta, Leu)}$), 14.1 ($CH_{2, butyl}$); IR: 3437, 3385, 3288, 3207, 1687, 1652, 1615, 1519.

EXAMPLE 10

N-hexyloxalamido-L-leucylamide (11)

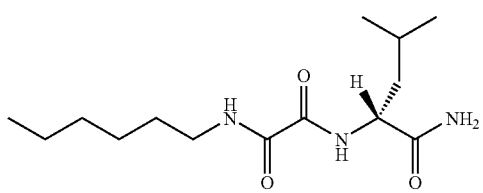

Molecular Weight = 285,39
Molecular Formula = C14H27N3O3

The solution of N-hexyloxalamido-L-leucine methyl ester (5) (0.375 g, 1.248 mmol) in $CH_2Cl_2$ (1 ml) and conc. $NH_3$/MeOH (30 ml) was kept for 7 days at 4-8° C. The precipitate was filtered off, washed with MeOH. Yield: 86.2%; $^1H$ NMR (DMSO-$d_6$): δ 8.78 (1H, t, J=6.0, $NH_{hexyl}$), 8.37 (1H, d, J=9.0, $NH_{Leu}$), 7.48, 7.11 (2×1H, 2 s, $CONH_2$), 4.28 (1 H, dt, J=9.2, J=3.9, $CH_{\alpha, Leu}$), 3.17-3.07 (2 H, m, $CH_2N$), 1.72-1.14 (11 H, m, $CH_\alpha$, $CH_{2(\beta, Leu)}$, $CH_{2, hexyl}$), 0.92-0.80 (9 H, m, $CH_{3(\gamma, Leu)}$ and $CH_{3, hexyl}$); $^{13}C$ NMR (DMSO-$d_6$): δ 173.6 ($CONH_2$), 160.05, 159.99 (CON), 51.8 ($CH_{\alpha, Leu}$), 41.4, 39.4 ($CH_{2(3, Leu)}$, $CH_{2, hexyl}$), 31.4, 29.1, 26.4, 22.5 ($CH_{2, hexyl}$), 24.8 ($CH_{\alpha, Leu}$), 23.5, 21.9 ($CH_{2(\beta, Leu)}$), 14.3 ($CH_{2, hexyl}$); IR: 3432, 3385, 3287, 3208, 1685, 1652, 1515.

EXAMPLE 11

N-hexyloxalamido-L-phenylalaninamide (12)

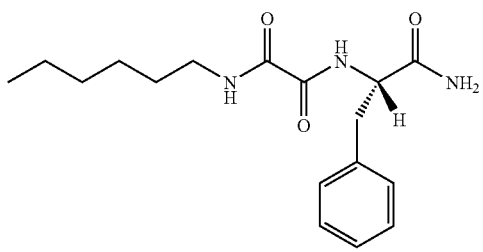

Molecular Weight = 319,41
Molecular Formula = C17H25N3O3

The solution of N-hexyloxalamido-L-phenylalanine methyl ester (6) (0.023 g, 0.0658 mmol) in $CH_2Cl_2$ (0.5 ml) and conc. $NH_3$/MeOH (5 ml) was kept for 7 days at 4-8° C. The precipitate was filtered off, washed with MeOH. Yield: 80.9%; $^1H$ NMR (DMSO-$d_6$): δ 8.67 8.67 (1 H, t, J=5.9, $NH_{hexyl}$), 8.37 (1 H, d, J=8.7, $NH_{hexyl}$), 7.58, 7.25 (2H, 2 s, $CONH_2$), 7. 28-7.13 (5 H, m, $CH_{arom}$), 4.47 (1H, dt, J=4.5, J=8.9, $CH_{\alpha, Phe}$), 3.13-3.03 (4 H, m, $CH_2N$ and $CH_{2A(\beta, Phe)}$), 2.99 (1H, dd, J=9.2, J=13.7, $CH_{2B(\beta, Phe)}$), 146-1.37, 1.29-1.15 (2 H and 6 H, 2m, $CH_{2, hexyl}$), 0.85 (3 H, t, J=6.9, $CH_{3, hexyl}$), $^{13}C$ NMR (DMSO-$d_6$): δ 171.9 ($CONH_2$), 159.4, 159.3 (CON), 137.5 ($C_{arom}$), 129.1, 128.0, 126.3 ($CH_{arom}$), 54.0 ($CH_{\alpha, Phe}$), 38.8, 35.2 ($CH_{2(\beta, Phe)}$ and $CH_2N$), 30.8, 28.6, 25.9, 22.0 ($CH_{2, hexyl}$), 13.8 $CH_{3, hexyl}$).

EXAMPLE 12

N-dodecyloxalamido-L-leucylamide (16)

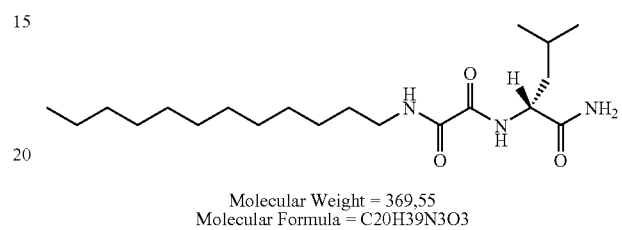

Molecular Weight = 369,55
Molecular Formula = C20H39N3O3

The solution of N-dodecyloxalamido-L-leucine methyl ester (13) (0.375 g, 0.975 mmol) in $CH_2Cl_2$ (1 ml) and conc. $NH_3$/MeOH (25 ml) was kept for 7 days at 4-8° C. The precipitate was filtered off, washed with MeOH. Yield 81.3%; $^1H$ NMR (DMSO-$d_6$): δ 8.78 (1 H, t, J=5.9, $NH_{dodecyl}$), 8.36 (1 H, d, J=9.1, $NH_{Leu}$), 7.49, 7.11 (2×1 H, 2 s, $CONH_2$), 4.28 (1H, dt, J=9.1, J=3.8, $CH_{\alpha, Leu}$), 3.18-3.02 (2 H, m, $CH_2N$), 1.72-1.09 (23 H, m, $CH_\alpha$, $CH_{2(\beta, Leu)}$, $CH_{2, decyl}$), 0.91-0.81 (9 H, m, $CH_{3(\gamma, Leu)}$ and $CH_{3, dodecyl}$) $^{13}C$ NMR (DMSO-$d_6$): δ 173.6 ($CONH_2$), 160.03, 159.99 (CON), 51.8 ($CH_\alpha$), 41.4, 39.4 ($CH_{2(\beta, Leu)}$, $CH_{2, dodecyl}$), 31.7, 29.50, 29.47, 29.45, 29.42, 29.17, 29.14, 29.11, 26.8, 22.6 ($CH_{2, decyl}$), 24.8 ($CH_{\gamma, Leu}$), 23.4, 22.0 ($CH_{3(\delta, Leu)}$), 14.4 ($CH_{2, dodecyl}$) IR: 3389, 3291, 3198, 1686, 1653, 1511.

Testing of Gelation Properties of Organogelators

The gelation properties of the compounds of the invention were tested and minimal gelation concentrations (m.g.c.) were determined. The results are shown in the Table 1. and Table 2.

Procedure

The experiments were performed by dissolution of the weighted amount of organogelators (10 mg) in a measured volume of selected solvent. In the first case, when pure solvent was used, heating of the sample was necessary to produce solution. By cooling the solution to room temperature gel was obtained. The portions of solvent were repeatedly added until the gel disappeared.

In the second case, when mixtures of solvent were used, the sample (10 mg) was dissolved in first solvent and measured volume (0.05-0.25 ml) of second solvent was added. Gel was formed by heating of this mixture followed by cooling. The portions of second solvent were repeatedly added until the gel disappeared. For very efficient organogelators m.g.c. was determined on amount of gelators ca. 2 mg.

In order to compare the gelation properties and chemical structures of the compounds, we tested their gelation properties in several organic solvents of different polarity, water and commercial fuels.

TABLE 1

Maximum solvent volume (in μl) that can be gelated by the specific amount (10 mg) of organogelators (amides and salts of carboxylic acids)

| | C4—NH₂ 4 | C6—NH₂ 11 | C6-Phe-NH₂ 12 | C12—NH₂ 16 | C4—O⁻Na⁺ 3 | C6—O⁻Na⁺ 9 | C12—O⁻Na⁺ 15 |
|---|---|---|---|---|---|---|---|
| petrol | 45800 | 79200 | 7000 | 10300 | NG | NG | NG |
| diesel | 36100 | 67200 | 10000 | 42400 | NG | NG | NG |
| H₂O | 6850 | NG | NT | NG | NG | NG | NG |
| DMSO | NG | NG | NG | NG | NG | NG | NG |
| DMSO-H₂O | 1500 + 750 | 2150 + 1650 | 7500 + 20500 | 17100 + 20700 | NG | NG | NG |
| DMF-H₂O | 600 + 500 | 1150 + 2550 | 3450 + 3450 | 10350 + 13300 | NG | NG | NG |
| EtOH | 250 | NG | NG | 1050 | NG | NG | NG |
| THF | 100 | NG | 500 | 150 | NG | NG | NG |
| EtOAc | 200 | NG | 1000 | NG | NG | NG | NG |
| acetone | NG | NG | NG | NG | NG | NG | NG |
| CH₂Cl₂ | 1050 | 750 | NT | 750 | NG | NG | NG |
| CH₂Cl₂-DMSO | | | 400 + 40 | | | | |
| CH₃CN | NG | NG | NG | 1450 | NG | NG | NG |
| toluene | 24950 | 16200 | 4000 | 15200 | NG | NG | NG |
| p-xylene | 33600 | 68000 | 7000 | 5250 | NG | NG | NG |
| decaline | 37400 | 106250 | 26000 | 24100 | NG | NG | NG |
| tetraline | 500 | 150 | 500 | 300 | NG | NG | NG |

TABLE 2

Maximum solvent volume (in μl) that can be gelated by the specific amount (10 mg) of organogelators (esters and carboxylic acids)

| | C4—OMe 1 | C6—OMe 5 | C6-Phe-OMe 6 | C12—OMe 13 | C4—OH 2 | C6—OH 7 | C6-Phe-OH 8 | C12—OH 14 |
|---|---|---|---|---|---|---|---|---|
| petrol | NG | NG | 400 | NG | NG | NG | 6500 | NG |
| diesel | NG | NG | 5750 | NG | NG | NG | 5750 | NG |
| H₂O | NG | NG | NG | NG | NG | NG | 10750 | NG |
| DMSO | NG | NG | NG | NG | NG | NG | NG | 550 |
| DMSO-H₂O | NG | NG | 9430 + 11750 | 2720 + 3050 | NG | 250 + 450 | 170 + 11750 | NG |
| DMF-H₂O | NG | NG | 5150 + 3350 | 14100 + 20700 | NG | NG | 550 + 7500 | NG |
| EtOH | NG | NG | NG | NG | NG | NG | NG | NG |
| THF | NG | NG | NG | NG | NG | NG | NG | NG |
| EtOAc | NG | NG | NG | NG | NG | NG | NG | NG |
| EtOAc + hexane | | | | | | | 200 + 1500 | |
| acetone | NG | NG | NG | NG | NG | NG | NG | NG |
| CH₂Cl₂ | NG | NG | NG | NG | NG | NG | NG | NG |
| CH₂Cl₂ + hexane | | | | | | | 2750 + 8750 | |
| CH₃CN | NG | NG | NG | NG | NG | NG | NG | NG |
| toluene | NG | NG | NG | NG | NG | NG | 2500 | NG |
| p-xylene | NG | NG | 100 | NG | NG | NG | 4250 | NG |
| decaline | NG | NG | 4300 | NG | NG | NG | 6950 | NG |
| tetraline | NG | NG | NG | NG | NG | NG | NG | NG |

The invention claimed is:

1. A gel comprising a compound of general formula (I):

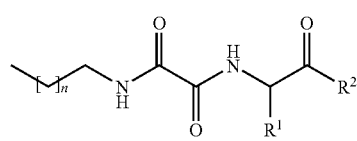

(I)

wherein:
R¹ is hydrogen, phenyl, $C_{1-6}$ alkyl which can be further optionally substituted with R³
wherein R³ is 5 or 6 member aromatic or heteroaromatic ring system which can be further optionally substituted with benzyl or hydroxy:
R² is OR⁴, NHR⁴
wherein R⁴ is hydrogen, $C_{1-6}$ alkyl or benzyl
n is an integer from 1 to 12
or a salt thereof.

2. The gel comprising the compound as claimed in claim 1, wherein independently or in any combination:
R¹ is isobutyl
R² is OR⁴, OH, NHR⁴
n is an integer of 1 to 10
or a salt thereof.

3. The gel comprising the compound of general formula (I) as claimed in claim 1, wherein R² is NH₂ and n is 2 to 10.

4. The gel comprising the compound as claimed in claim 2 wherein R² is OR⁴.

5. The gel comprising the compound as claimed in claim 1 wherein R² is OH.

6. The gel comprising the compound as claimed in claim 1 wherein R² is NHR⁴.

7. The gel comprising the compound of claim 1, wherein the group R¹ is isobutyl group.

8. The gel comprising the compound of claim 1, wherein the compound is a sodium salt.

9. The gel comprising the compound of claim 1, wherein the salt is a salt of ammonium or salt of $C_{1-6}$ alkyl or benzyl amine.

10. The gel comprising the compound of claim 1, selected from the group consisting of N-Butyloxalamido-L-leucine methyl ester, N-Butyloxalamido-L-leucine, N-Butyloxalamido-L-leucine sodium salt, N-Butyloxalamido-L-leucylamide, N-hexyloxalamido-L-leucine methyl ester, N-hexyloxalamido-L-phenylalanine methyl ester, N-hexyloxalamido-L-leucine, N-hexyloxalamido-L-phenylalanine, N-hexyloxalamido-L-leucine sodium salt, N-hexyloxalamido-L-phenylalanine sodium salt, N-hexyloxalamido-L-leucylamide, N-hexyloxalamido-L-phenylalaninamine, N-dodecyloxalamido-L-leucine methyl ester, N-dodecyloxalamido-L-leucine, N-dodecyloxalamido-L-leucine sodium salt, and N-dodecyloxalamido-L-leucylamide.

11. The gel as claimed in claim 1, wherein the process for preparing the gel comprises dissolving the compound in a solvent.

12. The gel according to claim 11, wherein the solvent can be selected from one of the following: commercial fuel, organic solvent, water and a mixture of water with organic solvent.

13. The gel according to claim 12, wherein the commercial fuel can be petrol, or diesel.

14. The gel according to claim 12, wherein the organic solvent can be selected from the group consisting of DMSO, DMF, EtOH, $CH_3CN$, THF, $CH_2Cl_2$, acetone, toluene, p-xylene, tetraline, and decaline.

15. The gel according to claim 12, wherein the solvent is a mixture of water with DMSO, or DMF.

16. The gel according to claim 12, wherein the solvent is water.

* * * * *